Oct. 17, 1967 L. O. MUGG Plant Pat. 2,771
ALMOND
Filed Aug. 18, 1966
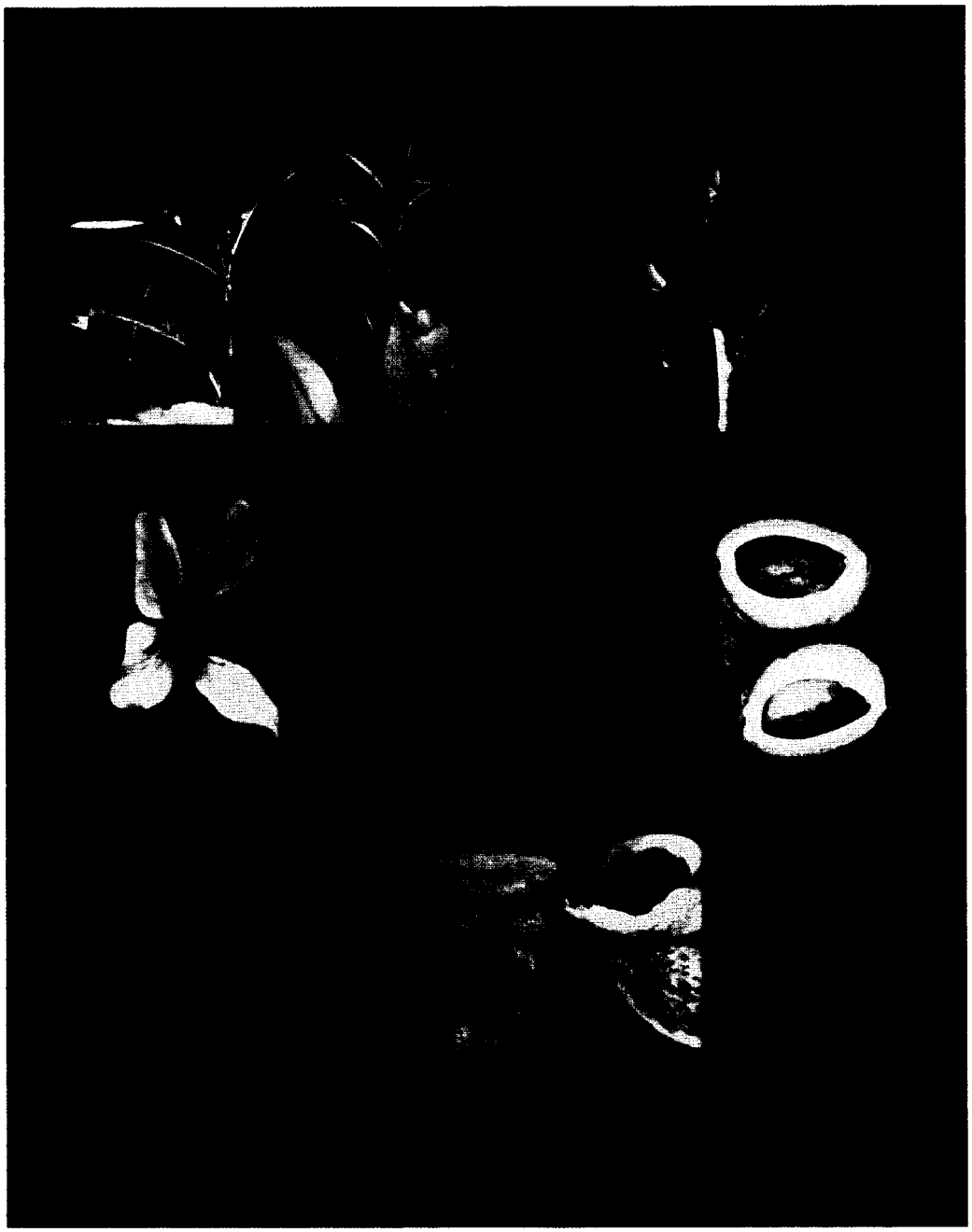
INVENTOR
Leland O. Mugg
BY
Fleh & Swain
Attorneys United States Patent Office Plant Pat. 2,771
Patented Oct. 17, 1967

2,771
ALMOND

Leland O. Mugg, Wasco, Calif., assignor to Kern County Land Company, San Francisco, Calif.

Filed Aug. 18, 1966, Ser. No. 573,433
1 Claim. (Cl. Plt.—30)

This discovery relates to a new and distinct variety of almond tree which was discovered as a mutation. The mutation was a bud sport of a mature Nonpareil on S-37 rootstock growing in a cultivated orchard in Kern County, Calif.

After discovery, the new variety was asexually reproduced at Kernland Orchards in Kern County, Calif. Such asexual reproduction was accomplished by top working on older trees. It was found that the asexual reproduction continued the characteristics of the parent in all respects.

The newly discovered variety of almond tree is distinctively characterized in comparison with the Nonpareil in that its blossoms are red as contrasted to the white of Nonpareil. Furthermore, the skin of the immature kernel is red.

The tree is vigorous and is similar to the Nonpareil in size and shape. The crop is regular and heavy and is approximately two days later than the Nonpareil.

The nut is paper-shelled and is slightly smaller than, but of similar shape to the Nonpareil.

The drawing is in the form of a photographic reproduction illustrating, from left to right and top to bottom: the foilage, a bud, a blossom, an immature nut including kernel and broken away shell and a mature nut including an open hull.

Referring to the details of the new and distinct variety, the following is a description thereof in outline form. Specifications of color refer to the Nickerson Color Fan, Maximum Chroma 40 hues, published 1957 by Munsell Color Company, Baltimore, Md., and distributed by the American Horticultural Society.

Tree:
- *Density.*—Similar to Nonpareil, open.
- *Size.*—Same as Nonpareil.
- *Shape.*—Similar to Nonpareil.
- *Vigor.*—Vigorous.

Trunk:
- *Form.*—Medium.
- *Texture.*—Like Nonpareil.
- *Color of bark.*—4YR 4/5.

Branches:
- *Form.*—Medium.
- *Strength.*—Same as Nonpareil.
- *Texture.*—Medium.
- *Lenticels.*—Same as Nonpareil.
- *Branching habit.*—Spreading.
- *Color.*—(a) Mature wood—9YR 5/4 to 5/6. (b) New wood—10GY 7/8 to 8/5. (c) New terminal stem growth—2.5R 3/7.

Foliage:
- *Quantity.*—Medium.
- *Susceptibility, or resistance to insects or disease.*—Same as Nonpareil.

Leaves:
- *Size.*—Medium.
- *Average length (without petiole).*—3 inches.
- *Average width.*—⅞ inch.
- *Shape.*—Pointed, lanceolate.
- *Distribution.*—Well distributed.
- *Thickness.*—Thin.
- *Texture.*—Smooth.
- *Margin.*—Shallow crenations.
- *Petiole.*—Long, thin.

Glands:
- *Average number.*—2 (varying from 1 to 3).
- *Position.*—Alternate, on petiole and base of leaf.
- *Size.*—Small.
- *Form.*—Globose.

Stipules:
- *Size.*—3/16 inch long.
- *Shape.*—Pointed, serrated.

Leaf color:
- (a) *Growing season.*—(1) Upper side—5GY 4/2. (2) Under side—5.5GY 4/3. (3) New terminal leaves—2.5R 3/7.
- (b) *At harvest.*—(1) Upper side—7.5GY 4/4 value color tends to yellow 5/7. (2) Under side—7.5GY 4/4 value with gray cast.

Bloom:
- *Amount of bloom.*—Heavy.
- *Shape before unfolding.*—Spherical.
- *Color.*—5R 8/6 blending to 5R 7/9.
- *Blooming period.*—2 days later than Nonpareil.

Crop:
- *Bearing.*—Regular.
- *Productivity.*—Heavy.
- *Distribution of nuts on tree.*—Well distributed; few clusters.
- *Harvest period.*—2 days later than Nonpareil.
- *Tenacity.*—Hang well on tree.

Hull:
- *Outer surface.*—Slightly rougher than Nonpareil.
- *Pits.*—No.
- *Form.*—Regular.
- *Thickness.*—Thick.
- *Flesh.*—Tough.
- *Suture.*—Ridged.
- *Color.*—(a) During growing season—a bit darker than Nonpareil 10GY 6/9. (b) At harvest—12Y 9/9–2.5GY 9/8.
- *Dihiscense.*—Freely.
- *Splitting.*—Suture.

Nut:
- *Size.*—Medium.
- *Average length.*—1¼ inches.
- *Average thickness.*—½ inch.
- *Average width.*—¾ inch.
- *Nuts per pound on average sample.*—300; very dry.
- *Form.*—(a) Length/width—elongated. (b) Width/thickness—medium.
- *Shell.*—Paper. (a) Outer shell—crumbling. (b) inner shell—soft, well sealed.
- *Shell color.*—7.5YR 5/7 to 7.5YR 9/4. Majority between 7.5YR 1/4–7.5YR 8/8.
- *Pits.*—Large, sparce, shallow.
- *Stem scar.*—Small.
- *Apex.*—Acute.
- *Wing.*—Thin, broad—extends entire length.
- *Inner surface color.*—Light 7.5RP 4/11. Varigated on 7.5YR 7/11 background. (a) Ventral streak shape—broad, long. (b) Ventral streak color—2.5YR 5/9.
- *Percent of kernel to nut on average samples.*—93.

Kernel:
- *Size.*—Medium.
- *Average length.*—⅞ inch.
- *Average width.*—7/16 inch.
- *Average thickness.*—¼ inch.
- *Kernels per ounce on average sample.*—20.
- *Form.*—(a) Length/width—elongated. (b) width/thickness—medium.
- *Base.*—Slightly ventrally oblique.
- *Stem scar.*—Medium to large.
- *Apex.*—Acute slight recurve.

*Surface.*—Relatively smooth.
*Pellicle.*—Thin.
*Pubescence.*—Smooth.
*Color of immature kernel.*—3R between 4/10 and 5/12 stippled onto background of white.
*Color of mature kernel.*—10RP 3/10 stippled onto background of 10YR 5/6.
*Number of doubles.*—None.
*Number of defective kernels.*—Few.
*Flavor.*—Sweet.
*Quality.*—Excellent.

Pollenation:

*Self-pollenizing.*—No.
*Cross-pollenation with known variety.*—Requires same pollinators as Nonpareil.

*What varities.*—Primarily Mission and Davy. However, NePlus and Kapareil are also considered as pollinators of Nonpareil.

The variety described herein may vary in slight details due to climatic and soil conditions under which it may be grown. The present description is of the variety as grown in Kern County, Calif., at the Kernland Orchards.

The following is claimed:

A new and distinct variety of almond tree, as illustrated and described, characterized by red blooms and nuts.

No references cited.

ABRAHAM G. STONE, *Primary Examiner.*
ROBERT E. BAGWILL, *Examiner.*